US005646020A

United States Patent [19]
Swiggen et al.

[11] Patent Number: 5,646,020
[45] Date of Patent: Jul. 8, 1997

[54] HAMMERHEAD RIBOZYMES FOR PREFERRED TARGETS

[75] Inventors: James A. Swiggen, Solon; J. Anthony Mamone, Parma, both of Ohio

[73] Assignee: Ribozyme Pharmaceuticals, Inc., Cleveland, Ohio

[21] Appl. No.: 166,664

[22] Filed: Dec. 10, 1993

Related U.S. Application Data

[63] Continuation of Ser. No. 884,074, May 19, 1992, abandoned.

[51] Int. Cl.⁶ .................................................. C12P 19/34
[52] U.S. Cl. ........................................ 435/91.31; 435/172.1
[58] Field of Search ............................. 435/91.1, 91.3, 435/91.31, 172.1, 6, 7.1

[56] References Cited

PUBLICATIONS

Haseloff et al, Nature, V. 334, Aug.18 1988, p. 585.
Taylor, et al., "Ribozyme–Mediated Cleavage of an HIV–1 gag RNA: The Effects of Nontargeted Sequences and Secondary Structure on Ribozyme Cleavage Activity", 1 *Antisense Res and Dev* 173, 1991.
Sambrook, et al., "Molecular Cloning: A Laboratory Manual", published by Cold Spring Harbor Laboratory Press (N.Y.), pp. 7.71 –7.78, 1989.
Scanlon et al., "Ribozyme–mediated cleavage of c–fos mRNA reduces gene expression of DNA synthesis enzymes and metallothionein", 88 *Proc. Natl. Acad. Sci.*10591, 1991.
Usman et al., "Automated Chemical Synthesis of Long Oligoribonucleotides Using 2'–O–Silylated Ribonucleoside 3'–O–Phosphoramidites on a Controlled–Pore Glass Support: Synthesis of 43–Nucleotide Sequence Similar to the 3'–Half Molecule of an *Escherichia coli* Formylmethionine tRNA", 109 *Jrnl of Amer. Chem, Society*, 7845, 1987.
Slim et al., "Configurationally Defined Phosphorothioate––Containing Oligoribonucleotides in the Study of the Mechanism of Cleavage of Hammerhead Ribozymes", 19 *Nucl Acids Res.* 1183, 1991.

Cameron et al., "Specific Gene Expression by Engineered Ribozymes in Monkey Cells", 86 *Proc Natl. Acad. Sci.* 9139, 1989.
Dropulic, et al., "Functional Characterization of a U5 Ribozyme: Intracellular Suppression of Human Immunodeficiency Virus Type 1 Expression", 66 *Jrnl of Virol.* 1432, 1992.
Tsukiyama–Kohara et al., "Internal Ribosome Entry Site within Hepatitis C Virus RNA", 66 *Jrnl of Virol.* 1476, 1992.
Perrotta and Been, 31 *Biochemistry* 16, 1992, "Cleavage of Oligoribonucleotides by a Ribozyme Derived from the Hepatitis δ Virus RNA Sequence".
Hampel and Tritz, 28 *Biochemistry* 4929, 1989, "RNA Catalytic Properties of the Minimum (–)sTRSV Sequence".
Hampel et al., 18 *Nucleic Acids Research* 299, 1990, "'Hairpin' Catalytic RNA Model: Evidence for Helices and Sequence Requirement for Substrate RNA".
Heidenreich and Eckstein, 267 *Journal of Biological Chemistry* 1904, 1992, "Hammerhead Ribozyme–mediated Cleavage of the Long Terminal Repeat RNA of Human Immunodeficiency Virus Type 1".
Weerasinghe et al., 65 *Journal of Virology* 5531, 1991, "Resistance to Human Immunodeficiency Virus Type 1 (HIV–1) Infection in Human CD4⁺ Lymphocyte–Derived Cell Lines Conferred by Using Retroviral Vectors Expressing an HIV–1 RNA–Specific Ribozyme".
Mamone et al., "Design of Hammerhead Ribozymes Targeted to Sequences in HIV, HSV, and the RAT ANF GENE", Abstract of Keystone, CO (May 27, 1992).
Pavco et al., "Regulation of Self–Splicing Reactions by Antisense RNA", Abstract of Keystone, CO (May 27, 1992).
Haseloff and Gerlach, 334 *Nature* 585, 1988, "Simple RNA Enzymes with New and Highly Specific Endoribonuclease Activities".

*Primary Examiner*—David Guzo
*Attorney, Agent, or Firm*—Lyon & Lyon LLP

[57] ABSTRACT

A method for selecting a hammerhead ribozyme target site comprising the step of selecting a site comprising an XXUH/XX nucleotide sequence, where XX are strong duplex forming bases, H is U, A or C, and the slash represents the cleavage site.

43 Claims, 1 Drawing Sheet

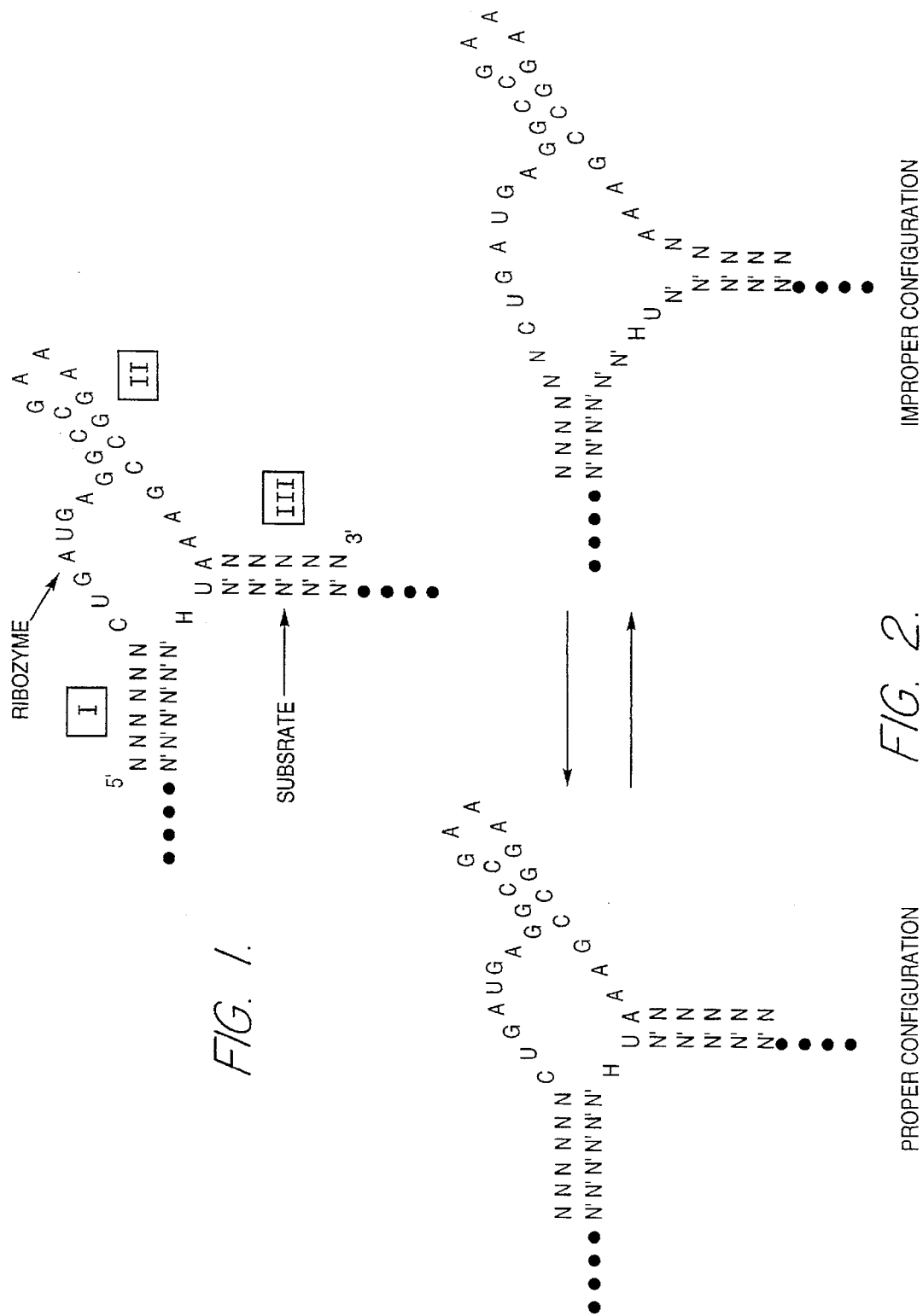

HAMMERHEAD RIBOZYMES FOR PREFERRED TARGETS

This application is a continuation of application Ser. No. 07/884,074, filed May 14, 1992 now abandoned.

BACKGROUND OF THE INVENTION

This invention relates to hammerhead ribozymes and their interaction with substrate RNA.

Hammerhead ribozymes are generally described by Haseloff and Gerlach (1988) *Nature*, 334, 555. In this article, the design of new ribozymes and testing of a synthetic ribozyme is discussed, as well as their application in vitro and in vivo. FIG. 1 is a diagrammatic representation of a hammerhead ribozyme and its substrate (where N represents any nucleotide, H represents A, U or C, and I, II and III represent various stems of the ribozyme); the closed circles represent nucleotide bases in the substrate.

SUMMARY OF THE INVENTION

This invention features an improved method for designing active hammerhead ribozymes. Such ribozymes are chosen to include sequences which form "strong" base-pairing interactions at the positions closest to the internal loop formed by the ribozyme-substrate complex (parameters for sequence-specific duplex stability are found in Freier, et al. "Improved Parameters for Predictions of RNA Duplex Stability" (1986) *Proc. Nat. Acad. Sci. (USA)*, 83, 9373–9377). Thus, such ribozymes have a substrate sequence XXUH/XX (where XX are "strong" duplex forming bases, H is U, A or C, and the slash represents the cleavage site) "Strong" duplex forming bases are chosen to be those which have dinucleotide free energies of helix propagation of −2.0 kcal/mole or less (i.e. GA, UC, GU, AC, CG, GC, GG, CC; see Freier, et el). Such ribozymes are more active than other ribozymes having "weak" duplex forming bases at the positions XX. These ribozymes are more efficient at cleaving the substrate RNA molecules since the ribozyme is able to bind to the substrate tightly enough to allow the catalytic components to be positioned for cleavage, but is still weakly enough bound to allow the reaction to be driven to completion by dissociation of the product RNA. Provision of strong ribozyme-substrate interactions at these positions allows for maximal cleavage activity by forming a rigid structure close to the central loop of the ribozyme. This prevents the interior portions of stems I and III of the ribozyme from separating prematurely due to local thermal fluctuations. FIG. 2 is a diagrammatic representation of the equilibrium between a tightly constrained structure ("Proper configuration") and an undesirable loose structure ("Improper configuration"). The method of this invention is to select ribozymes and substrates which maximize the proper configuration.

Stem III is limited in this regard since the innermost base-pair must be AU with the U in the substrate. Stem I, however, has no such constraints and ribozymes can be chosen which include "strong" duplex forming bases immediately adjacent to the internal loop.

Thus, in a first aspect, the invention features a method for providing a more active hammerhead ribozyme by modifying the ribozyme to have "strong" duplex forming bases at the variable positions closest to the internal loop.

In a second related aspect, the invention features a method for selecting a substrate or target site at which a hammerhead ribozyme will be more active. The method includes the step of selecting a substrate site having the sequence XXUH/XX (where XX are "strong" duplex forming bases, H is U, A or C, and the slash represents the cleavage site).

Other features and advantages of the invention will be apparent from the following description of the preferred embodiments thereof, and from the claims.

DESCRIPTION OF THE PREFERRED EMBODIMENTS

The drawings will first briefly be described.

Drawings:

FIG. 1 is a diagramatic representation of a hammerhead ribozyme and its substrate (SEQ ID NO: 21).

FIG. 2 is a diagramatic representation of a hammerhead ribozyme (SEQ ID NO: 21) in equilibrium between a tightly constrained structure and an undesirable loose structure.

EXAMPLE

HIV-1 HSV AND ANF TARGETED RIBOZYMES

The following is data obtained from various ribozymes demonstrating the desirability of ribozymes having strong duplex forming bases at the variable positions closest to the internal loop.

Tables I, II and III contain sequence and activity information for ribozymes designed against targets found in the HIV-1 genome, the HSV genome, and the rat ANF gene, respectively. Activities (as $kcat/k_M$) were determined by incubating 2–100nM ribozyme with approximately 1 nM radioactively labeled substrate for different times in 75 mM Tris-HCl pH 8.0, 10 mM $MgCl_2$. The products are separated by denaturing polyacrylamide electrophoresis and quantitated by a beta emission scanner (Ambis Systems, San Diego, Calif.). The data are treated per Michaelis-Menton for excess enzyme, specifically, the negative log of the fraction substrate remaining is plotted as a function of time. The resulting slope is then plotted as a function of ribozyme concentration. The slope of this line is then $kcat/k_M$.

Ribozymes which meet the strong base-pair criteria for stem I are marked with a "I" in the left margin. The average activity of these ribozymes is $33 \times 10^6$/M·min, which is well above the average for all the represented ribozymes ($22 \times 10^6$/M·min) and the average for ribozymes not meeting this criteria ($15 \times 10^6$/M·min). Ribozymes which meet the strong base-pair criteria for stem III are marked with a "III" in the left margin. The average activity of these ribozymes is $28 \times 10^6$/M·min, and for those not meeting this criteria is $8 \times 10^6$ M·min. Six ribozymes have the appropriate strong inner bases in both stems. Their average activity is $37 \times 10^6$/M·min. See, McSwiggen, entitled "Hammerhead Ribozymes", filed on the same day as the present application, and assigned to the same assignee, the whole of which (including drawings) is hereby incorporated by reference herein, which describes a method for determining ribozyme activity. This application has been assigned Ser. No. 07/884,422.

TABLE I

Summary of HIV ribozyme activity

| | Ribozyme | Stem III (3' RZ) length (bp) | ΔG° (kcal/mole) | Sequence | Stem I (5' RZ) length (bp) | ΔG° (kcal/mole) | Sequence | Total ΔG of Binding (kcal/mole) | kcal/kM (/10^6 M · min) |
|---|---|---|---|---|---|---|---|---|---|
| | HCH-r36 | 5 | −7 | ACUUC | 5 | −9.7 | (GG)AGGCU | −6.0 | 0.17 |
| | HCH-r38 | 6 | −9.9 | ACUUCC | 6 | −10.8 | (GG)UAGGCU | −10.1 | 6.0 |
| | HCH-r40 | 7 | −11.6 | ACUUCCU | 7 | −11.7 | (GG)UUAGGCU | −12.8 | 5.4 |
| | HCH-r42 | 8 | −13.4 | ACUUCCUG | 8 | −12.6 | (GG)UUUAGGCU | −15.4 | 3.3 |
| | HCH-r37-5' | 6 | −9.9 | ACUUCC | 5 | −9.7 | (GG)AGGCU | −9.1 | 0.54 |
| | HCH-r37-3' | 5 | −9.2 | ACUUC | 6 | −10.8 | (GG)UAGGCU | −7.0 | <0.01 |
| | HCH-r39-5' | 7 | −11.5 | ACGCU | 6 | −10.8 | (GG)UAGGCU | −11.9 | 7.0 |
| | HCH-r39-3' | 6 | −9.9 | ACUUCC | 7 | −11.7 | (GG)UUAGGCU | −11.0 | 14 |
| | HBH-r I | 5 | −9.2 | ACGCU | 4 | −5.7 | (GGAG)UACU | −3.4 | 0.006 |
| | HBH-r II | 5 | −7 | ACGCU | 8 | −8.7 | UUAAUACU | −7.3 | 0.58 |
| III | HBH-r III | 6 | −11.6 | ACUUCCU | 8 | −8.7 | UUAAUACU | −9.4 | 7.0 |
| | HBH-r IV | 6 | −11.5 | ACGCUC | 6 | −6.7 | AAUACU | −7.3 | 15.7 |
| | HBH-r V | 6 | −11.5 | ACGCUC | 7 | −7.8 | UAAUACU | −8.5 | 5.6 |
| | HBH-r VI | 6 | −11.5 | ACGCUC | 5 | −5.8 | AUACU | −6.4 | 3.15 |
| | HDH-34-MF | 6 | −11.9 | ACUGCC | 6 | −10.1 | GAGUCU | −10.2 | 16 |
| | HEH-34-MF | 6 | −9.6 | AGUCUG | 6 | −7.6 | CUUGAU | −5.4 | 1.1 |
| | HFH-34-MF | 6 | −7.7 | AUAGAG | 6 | −8.7 | UGCUUU | −4.6 | 1.2 |

| Substrate | Sequence |
|---|---|
| HCS-r29ch | GGAGCAUCCAGGAAGUCAGCCUAAAACUG (SEQ ID NO: 1) |
| HBS-r21 | UGCGAGAGCGUCAGUAUUAAG (SEQ ID NO: 2) |
| HDS-r13 | GGCAGUCAGACUC (SEQ ID NO: 3) |
| HES-r13 | CAGACUCAUCAAG (SEQ ID NO: 4) |
| HFS-r13 | CUCUAUCAAAGCA (SEQ ID NO: 5) |

TABLE II

HSV Summary

| | Ribozyme | Stem III (3' RZ) length (bp) | ΔG° (kcal/mole) | Sequence | Stem I (5' RZ) length (bp) | ΔG° (kcal/mole) | Sequence | Total ΔG of Binding (kcal/mole) | kcat/Km (/M · min) | Multiple kcat (/min) | Turnover Km (nM) |
|---|---|---|---|---|---|---|---|---|---|---|---|
| III | VAH-r36 | 6 | −11.4 | ACGGUC | 6 | −11.5 | GCGUCU | −12.4 | 20 | | |
| I,IV | VCH-r34 | 6 | −12.8 | ACCCCG | 6 | −11.7 | CCCACG | −13.4 | 68 | 1.73 | 34 |
| VI | VEH-r34 | 6 | −12.2 | ACGCCA | 6 | −10.1 | UUCUCC | −11.8 | 30 | | |
| I,III | VEH-r32 | 5 | −10.4 | ACGCC | 5 | −9.2 | UCUCC | −9.1 | 38 | | |
| III | VFH-r34 | 6 | −11 | ACGAGG | 6 | −10.4 | GACGAG | −9.7 | 3.4 | | |
| I,III | VGH-r35 | 6 | −11 | ACGAGG | 6 | −9.3 | CGGAC | −11.4 | 61 | 5.69 | 126 |
| III | VIH-r34 | 6 | −13.7 | ACCCCC | 6 | −10.6 | CGCGAA | −13.3 | 50 | 2.2 | 69 |
| I | VJH-r33 | 6 | −10.8 | ACAGCA | 5 | −9.9 | CCCGU | −9.3 | 5.6 (X10^6) | | |

| Substrate | Sequence |
|---|---|
| VAS-r17-2 | CAGACCGUCAGACGCUC (SEQ ID NO: 6) |
| VCS-r17 | GUCGGGGUCCGUGGGUC (SEQ ID NO: 7) |
| VES-r17 | GAUGGCGUCGGAGAACA (SEQ ID NO: 8) |
| VFS-r15 | GUCCUCGUCCUCGUC (SEQ ID NO: 9) |
| VGS-r16 | GUCCUCGUCGUCCGCA (SEQ ID NO: 10) |
| VIS-r17 | CCGGGGGUCUUCGCGCG (SEQ ID NO: 11) |
| VJS-r14 | GGUGCUGUAACGGG (SEQ ID NO: 12) |

TABLE III

Summary of ANF ribozyme activity

|  | Ribozyme | Stem III (3' RZ) | | | Stem I (5' RZ) | | | Total ΔG of Binding (kcal/mole) | kcal/kM (/10⁶ M · min) | Exp. |
|---|---|---|---|---|---|---|---|---|---|---|
|  |  | length (bp) | ΔG° (kcal/mole) | Sequence | length (bp) | ΔG° (kcal/mole) | Sequence |  |  |  |
|  | ACH-r32 | 5 | −7 | ACUUC | 5 | −8.8 | GGGUU | −5.7 | 1.2 | 64-19 |
|  | ACH-r33-5' | 6 | −9.9 | ACUUCC | 5 | −8.8 | GGGUU | −8.6 | 0.54 | 64-23 |
|  | ACH-r33-3' | 5 | −7 | ACUUC | 6 | −10.8 | CGGGUU | −6.6 | 0.0011 | 64-30 |
|  | ACH-r34 | 6 | −9.9 | ACUUCC | 6 | −10.8 | CGGGUU | −9.5 | 7.8 | 64-20 |
|  | ACH-r35-5' | 7 | −12.8 | ACUUCCC | 6 | −10.8 | CGGGUU | −12.4 | 1.0 | 64-25,27 |
|  | ACH-r35-3' | 6 | −9.9 | ACUUCC | 7 | −12.9 | ACGGGUU | −11.0 | 7.5 | 64-26 |
|  | ACH-r36 | 7 | −12.8 | ACUUCCC | 7 | −12.9 | ACGGGUU | −13.9 | 0.87 | 64-28 |
|  | AHH-r34-57 | 5 | −9.9 | ACGGG | 7 | −10.6 | CACUGUA | −9.8 | 8.5 | 64-35 |
|  | AHH-r34-66 | 6 | −12.2 | ACGGGA | 6 | −8.8 | ACUGUA | −10.8 | <0.1 | 64-40 |
|  | AHH-r35-67 | 6 | −12.2 | ACGGGA | 7 | −10.6 | CACUGUA | −12.3 | 16 | 64-35 |
|  | AHH-r38-88 | 8 | −14 | ACGGGAUU | 8 | −14.0 | GCACUGUA | −18.8 | 21 | 64-36 |
|  | AAH-r35-67 | 6 | −10.9 | ACACCG | 7 | −10.5 | UGUGUUG | −10.6 | 0.1 | 64-42 |
| III | ABH-r33-65 | 6 | −10.8 | ACCUCA | 5 | −10.7 | GGCAU | −11.2 | 18 | 64-37 |
| I,III | ADH-r34-57 | 5 | −9.9 | ACGGG | 7 | −12.1 | UCUCUGA | −11.6 | 9.3 | 64-44 |
| III | AEH-r35-76 | 7 | −11.9 | ACCUUCG | 6 | −9.5 | CAGCUU | −10.1 | 13 | 64-43 |
| I,III | AIH-r34-66 | 6 | −13.3 | ACCGGC | 6 | −8.1 | AUCUUC | −11.2 | 8.1 | 64-38 |
| I,III | AJH-r34-57 | 5 | −10.8 | ACCCC | 7 | −11.1 | UCAAUCC | −10.8 | 46 | 64-41 |
|  |  |  |  |  |  |  |  |  | k2 =.069 /min | 113.2 |

| Substrate | Sequence |
|---|---|
| ACS-r15 | GGGAAGUCAACCCGU (SEQ ID NO: 13) |
| AHS-r19 | AAAUCCCGUAUACAGUGCG (SEQ ID NO: 14) |
| AAS-r16 | GCGGUGUCCAACACAG (SEQ ID NO: 15) |
| ABS-r14 | AUGAGGUCAUGCCU (SEQ ID NO: 16) |
| ADS-r15 | ACCCGUCUCAGAGAG (SEQ ID NO: 17) |
| AES-r16 | GCGAAGGUCAAGCUGC (SEQ ID NO: 18) |
| AIS-r15 | UGCCGGUAGAAGAUG (SEQ ID NO: 19) |
| AJS-r15 | GGGGGUAGGAUUGAC (SEQ ID NO: 20) |

Other embodiments are within the following claims.

---

We claim:

1. A method for synthesizing a hammerhead ribozyme, comprising the steps of:
    selecting a site in a substrate comprising a 5'-XXUH/YY-3' nucleotide sequence, wherein XX is selected from the group consisting of 5'-GA-3', 5'-UC-3', 5'-GU-3', 5'-AC-3', 5'-GC-3', 5'-GG-3', and 5'-CC-3'; and wherein YY is selected from the group consisting of 5'-GA-3', 5'-GU-3', 5'-AC-3', 5'-CG-3', 5'-GC-3', 5'-GG-3', and 5'-CC-3'; H is selected from the group consisting of U, A and C, and the / represents the cleavage site; and
    synthesizing a hammerhead ribozyme to said site in said substrate, wherein: (a) said hammerhead ribozyme comprises a substrate binding portion comprising two variable portions; (b) said ribozyme comprises an interior loop when said ribozyme is hybridized with said substrate by base pairing of the substrate with said substrate binding portion; (c) said variable portions are adjacent said interior loop with one portion on either side of said loop; and (d) said variable portions comprise bases complementary to said XX and YY in said site.

2. The method of claim 1 wherein XX is 5'-GA-3', and YY is 5'-GA-3'.
3. The method of claim 1 wherein XX is 5'-GA-3', and YY is 5'-GU-3'.
4. The method of claim 1 wherein XX is 5'-GA-3', and YY is 5'-AC-3.
5. The method of claim 1 wherein XX is 5'-GA-3', and YY is 5'-GC-3'.
6. The method of claim 1 wherein XX is 5'-GA-3', and YY is 5'-GG-3'.
7. The method of claim 1 wherein XX is 5'-GA-3', and YY is 5'-CC-3'.
8. The method of claim 1 wherein XX is 5'-UC-3', and YY is 5'-GA-3'.
9. The method of claim 1 wherein XX is 5'-UC-3', and YY is 5'-GU-3'.
10. The method of claim 1 wherein XX is 5'-UC-3', and YY is 5'-AC-3.
11. The method of claim 1 wherein XX is 5'-UC-3', and YY is 5'-GC-3'.
12. The method of claim 1 wherein XX is 5'-UC-3', and YY is 5'-GG-3'.
13. The method of claim 1 wherein XX is 5'-UC-3', and YY is 5'-CC-3'.
14. The method of claim 1 wherein XX is 5'-GU-3', and YY is 5'-GA-3'.
15. The method of claim 1 wherein XX is 5'-GU-3', and YY is 5'-GU-3'.
16. The method of claim 1 wherein XX is 5'-GU-3', and YY is 5'-AC-3.
17. The method of claim 1 wherein XX is 5'-GU-3', and YY is 5'-GC-3'.
18. The method of claim 1 wherein XX is 5'-GU-3', and YY is 5'-GG-3'.
19. The method of claim 1 wherein XX is 5'-GU-3', and YY is 5'-CC-3'.
20. The method of claim 1 wherein XX is 5'-AC-3', and YY is 5'-GA-3'.
21. The method of claim 1 wherein XX is 5'-AC-3', and YY is 5'-GU-3'.
22. The method of claim 1 wherein XX is 5'-AC-3', and YY is 5'-AC-3.
23. The method of claim 1 wherein XX is 5'-AC-3', and YY is 5'-GC-3'.
24. The method of claim 1 wherein XX is 5'-AC-3', and YY is 5'-GG-3'.
25. The method of claim 1 wherein XX is 5'-AC-3', and YY is 5'-CC-3'.
26. The method of claim 1 wherein XX is 5'-GC-3', and YY is 5'-GA-3'.
27. The method of claim 1 wherein XX is 5'-GC-3', and YY is 5'-GU-3'.
28. The method of claim 1 wherein XX is 5'-GC-3', and YY is 5'-AC-3.
29. The method of claim 1 wherein XX is 5'-GC-3', and YY is 5'-GC-3'.
30. The method of claim 1 wherein XX is 5'-GC-3', and YY is 5'-GG-3'.
31. The method of claim 1 wherein XX is 5'-GC-3', and YY is 5'-CC-3'.
32. The method of claim 1 wherein XX is 5'-GG-3', and YY is 5'-GA-3'.
33. The method of claim 1 wherein XX is 5'-GG-3', and YY is 5'-GU-3'.
34. The method of claim 1 wherein XX is 5'-GG-3', and YY is 5'-AC-3.
35. The method of claim 1 wherein XX is 5'-GG-3', and YY is 5'-GC-3'.
36. The method of claim 1 wherein XX is 5'-GG-3', and YY is 5'-GG-3'.
37. The method of claim 1 wherein XX is 5'-GG-3', and YY is 5'-CC-3'.
38. The method of claim 1 wherein XX is 5'-CC-3', and YY is 5'-GA-3'.

39. The method of claim 1 wherein XX is 5'-CC-3', and YY is 5'-GU-3'.

40. The method of claim 1 wherein XX is 5'-CC-3', and YY is 5'-AC-3.

41. The method of claim 1 wherein XX is 5'-CC-3', and YY is 5'-GC-3'.

42. The method of claim 1 wherein XX is 5'-CC-3', and YY is 5'-GG-3'.

43. The method of claim 1 wherein XX is 5'-CC-3', and YY is 5'-CC-3'.

* * * * *

UNITED STATES PATENT AND TRADEMARK OFFICE
CERTIFICATE OF CORRECTION

PATENT NO. : 5,646,020

DATED : July 8, 1997

INVENTOR(S) : JAMES A. MCSWIGGEN, J. ANTHONY MAMONE

It is certified that error appears in the above-identified patent and that said Letters Patent is hereby corrected as shown below:

Title page, item [75],

Inventor Name should be --McSwiggen-- not "Swiggen" in both places

Title page,

Under "Related U.S. Application Data", Line 1, Delete "May 19" and insert --May 14--

Column 3, Table I, Under the Heading "Stem III (3' RZ)", column entitled "Ribozyme", 9th and 10th entry, the bracket showing III should extend to these as well Column 3, Table I, Under the Heading "Stem III (3' RZ)", column entitled "$\Delta G°$ (kcal/mole)", 6th line down: Delete "-9.2" and insert -- -7 --

Column 3, Table I, Under the Heading "Stem III (3' RZ)", column entitled "$\Delta G°$ (kcal/mole)", 7th line down: Delete "-11.5   ACGCU" and insert -- -11.6   ACUUCCU--

Column 3, Table I, Under the Heading "Stem III (3' RZ)", column entitled "$\Delta G°$ (kcal/mole)", 10th line down: Delete "-7" and insert -- -9.2 --

Column 3, Table I, Under the Heading "Stem III (3' RZ)", column entitled "$\Delta G°$ (kcal/mole)", 11th line down: Delete "-11.6   ACUUCCU" and insert -- -11.5    ACGCUC --

UNITED STATES PATENT AND TRADEMARK OFFICE
CERTIFICATE OF CORRECTION

PATENT NO. : 5,646,020

DATED : July 8, 1997

INVENTOR(S) : JAMES A. MCSWIGGEN, J. ANTHONY MAMONE

It is certified that error appears in the above-identified patent and that said Letters Patent is hereby corrected as shown below:

Column 3, Table II, Under the Heading "Stem III (3' RZ)", 3rd entry of the 1st column, Delete "VI"

Column 3, Table II, Under the Heading "Stem I (5' RZ)", column entitled "length (bp)", 6th entry down: Delete "6" and insert --5--

Signed and Sealed this

Tenth Day of November 1998

Attest:

BRUCE LEHMAN

Attesting Officer       Commissioner of Patents and Trademarks

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
    ( A ) LENGTH: 29
    ( B ) TYPE: nucleic acid
    ( C ) STRANDEDNESS: single
    ( D ) TOPOLOGY: linear ( i i ) SEQUENCE DESCRIPTION: SEQ ID NO: 1:

GGAGCAUCCA GGAAGUCAGC CUAAAACUG          29

( 2 ) INFORMATION FOR SEQ ID NO: 2:

( i ) SEQUENCE CHARACTERISTICS:

( A ) LENGTH: 21
( B ) TYPE: nucleic acid
( C ) STRANDEDNESS: single
( D ) TOPOLOGY: linear ( i i ) SEQUENCE DESCRIPTION: SEQ ID NO: 2:

UGCGAGAGCG UCAGUAUUAA G                    21

( 2 ) INFORMATION FOR SEQ ID NO: 3:

( i ) SEQUENCE CHARACTERISTICS:
( A ) LENGTH: 13
( B ) TYPE: nucleic acid
( C ) STRANDEDNESS: single
( D ) TOPOLOGY: linear ( i i ) SEQUENCE DESCRIPTION: SEQ ID NO: 3:

GGCAGUCAGA CUC                              13

( 2 ) INFORMATION FOR SEQ ID NO: 4:

( i ) SEQUENCE CHARACTERISTICS:
( A ) LENGTH: 13
( B ) TYPE: nucleic acid
( C ) STRANDEDNESS: single
( D ) TOPOLOGY: linear ( i i ) SEQUENCE DESCRIPTION: SEQ ID NO: 4:

CAGACUCAUC AAG                              13

( 2 ) INFORMATION FOR SEQ ID NO: 5:

( i ) SEQUENCE CHARACTERISTICS:
( A ) LENGTH: 13
( B ) TYPE: nucleic acid
( C ) STRANDEDNESS: single
( D ) TOPOLOGY: linear ( i i ) SEQUENCE DESCRIPTION: SEQ ID NO: 5:

CUCUAUCAAA GCA                              13

( 2 ) INFORMATION FOR SEQ ID NO: 6:

( i ) SEQUENCE CHARACTERISTICS:
( A ) LENGTH: 17
( B ) TYPE: nucleic acid
( C ) STRANDEDNESS: single
( D ) TOPOLOGY: linear ( i i ) SEQUENCE DESCRIPTION: SEQ ID NO: 6:

CAGACCGUCA GACGCUC                          17

( 2 ) INFORMATION FOR SEQ ID NO: 7:

( i ) SEQUENCE CHARACTERISTICS:
( A ) LENGTH: 17
( B ) TYPE: nucleic acid
( C ) STRANDEDNESS: single
( D ) TOPOLOGY: linear ( i i ) SEQUENCE DESCRIPTION: SEQ ID NO: 7:

GUCGGGGUCC GUGGGUC                          17

( 2 ) INFORMATION FOR SEQ ID NO: 8:

( i ) SEQUENCE CHARACTERISTICS:
( A ) LENGTH: 17
( B ) TYPE: nucleic acid ( C ) STRANDEDNESS: single
        ( D ) TOPOLOGY: linear ( i i ) SEQUENCE DESCRIPTION: SEQ ID NO: 8:

GAUGGCGUCG GAGAACA                                          17

( 2 ) INFORMATION FOR SEQ ID NO: 9:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION: SEQ ID NO: 9:

GUCCUCGUCC UCGUC                                            15

( 2 ) INFORMATION FOR SEQ ID NO: 10:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION: SEQ ID NO: 10:

GUCCUCGUCG UCCGCA                                           16

( 2 ) INFORMATION FOR SEQ ID NO: 11:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i i ) SEQUENCE DESCRIPTION: SEQ ID NO: 11:

CCGGGGGUCU UCGCGCG                                          17

( 2 ) INFORMATION FOR SEQ ID NO: 12:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION: SEQ ID NO: 12:

GGUGCUGUAA CGGG                                             14

( 2 ) INFORMATION FOR SEQ ID NO: 13:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION: SEQ ID NO: 13:

GGGAAGUCAA CCCGU                                            15

( 2 ) INFORMATION FOR SEQ ID NO: 14:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) SEQUENCE DESCRIPTION: SEQ ID NO: 14:

AAAUCCCGUA UACAGUGCG                                                       1 9

( 2 ) INFORMATION FOR SEQ ID NO: 15:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION: SEQ ID NO: 15:

GCGGUGUCCA ACACAG                                                          1 6

( 2 ) INFORMATION FOR SEQ ID NO: 16:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION: SEQ ID NO: 16:

AUGAGGUCAU GCCU                                                            1 4

( 2 ) INFORMATION FOR SEQ ID NO: 17:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION: SEQ ID NO: 17:

ACCCGUCUCA GAGAG                                                           1 5

( 2 ) INFORMATION FOR SEQ ID NO: 18:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION: SEQ ID NO: 18:

GCGAAGGUCA AGCUGC                                                          1 6

( 2 ) INFORMATION FOR SEQ ID NO: 19:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION: SEQ ID NO: 19:

UGCCGGUAGA AGAUG                                                           1 5

( 2 ) INFORMATION FOR SEQ ID NO: 20:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION: SEQ ID NO: 20:

GGGGGUAGGA UUGAC                                            15

(2) INFORMATION FOR SEQ ID NO: 21:

(i) SEQUENCE CHARACTERISTICS:
        (A) LENGTH: 34
        (B) TYPE: nucleic acid
        (C) STRANDEDNESS: single
        (D) TOPOLOGY: linear (ix) FEATURE:
        (D) OTHER INFORMATION: The letter "N"
            stands for any base.

(ii) SEQUENCE DESCRIPTION: SEQ ID NO: 21:

NNNNNNCUGA UGAGGCCGAA AGGCCGAAAN NNNN              34